US010449390B2

(12) United States Patent
Lachaine et al.

(10) Patent No.: US 10,449,390 B2
(45) Date of Patent: Oct. 22, 2019

(54) FEATURE TRACKING USING ULTRASOUND

(71) Applicant: Elekta LTD., Montreal (CA)

(72) Inventors: Martin Emile Lachaine, Montreal (CA); Sebastien Tremblay, St. Jean-sur-Richelieu (CA); Fabienne Lathuiliere, Outremont (CA); Tony Falco, La Prairie (CA)

(73) Assignee: Elekta LTD, Montreal, Quebec (CA)

( * ) Notice: Subject to any disclaimer, the term of this patent is extended or adjusted under 35 U.S.C. 154(b) by 899 days.

(21) Appl. No.: 14/702,037

(22) Filed: May 1, 2015

(65) Prior Publication Data
US 2015/0375013 A1  Dec. 31, 2015

Related U.S. Application Data

(63) Continuation of application No. 12/956,991, filed on Nov. 30, 2010, now abandoned.
(Continued)

(51) Int. Cl.
*A61B 8/00* (2006.01)
*A61N 5/10* (2006.01)
(Continued)

(52) U.S. Cl.
CPC ............ *A61N 5/1067* (2013.01); *A61B 8/085* (2013.01); *A61B 8/4245* (2013.01); *A61B 8/483* (2013.01);
(Continued)

(58) Field of Classification Search
CPC .... A61B 2034/2055; A61B 2034/2063; A61B 2034/2065; A61B 2090/378; A61B 34/20;
(Continued)

(56) References Cited

U.S. PATENT DOCUMENTS 3,082,322 A   3/1963   Koerner et al.
3,777,124 A   12/1973  Pavkovich
(Continued)

FOREIGN PATENT DOCUMENTS

CA   2416887 A1   2/2002
CA   2621741 A1   3/2007
(Continued)

OTHER PUBLICATIONS

"U.S. Appl. No. 12/956,991, Advisory Action dated Apr. 8, 2015", 7 pgs.
(Continued)

*Primary Examiner* — Amanda Lauritzen Moher
(74) *Attorney, Agent, or Firm* — Schwegman Lundberg & Woessner, P.A.; Sanjay Agrawal

(57) ABSTRACT

Various implementations of the invention provide techniques and supporting systems that facilitate real-time or near-real-time ultrasound tracking for the purpose of calculating changes in anatomical features during a medical procedure. More specifically, anatomical features within a patient undergoing a medical procedure are tracked by obtaining temporally-distinct three dimensional ultrasound images that include the feature of interest and obtaining a targeted subset of ultrasound images focused on the feature. Based on the targeted subset of ultrasound images, a displacement of the feature is determined and image parameters used to obtain the targeted subset of ultrasound images are adjusted based on the displacement. This results in a time-based sequence of three dimensional images and targeted ultrasound images of the feature that identify changes in the position, size, location, and/or shape of the feature.

28 Claims, 8 Drawing Sheets

Related U.S. Application Data

(60) Provisional application No. 61/294,294, filed on Jan. 12, 2010, provisional application No. 61/323,064, filed on Apr. 12, 2010.

(51) Int. Cl.
*A61B 8/08* (2006.01)
*A61B 34/20* (2016.01)
*G06T 7/246* (2017.01)
*A61B 90/00* (2016.01)

(52) U.S. Cl.
CPC .......... *A61B 8/54* (2013.01); *A61B 8/58* (2013.01); *A61B 34/20* (2016.02); *A61N 5/1049* (2013.01); *G06T 7/251* (2017.01); *A61B 8/4263* (2013.01); *A61B 8/4461* (2013.01); *A61B 8/4472* (2013.01); *A61B 8/587* (2013.01); *A61B 2034/2055* (2016.02); *A61B 2034/2063* (2016.02); *A61B 2034/2065* (2016.02); *A61B 2090/378* (2016.02); *A61N 2005/1058* (2013.01); *A61N 2005/1074* (2013.01); *G06T 2207/10132* (2013.01); *G06T 2207/10136* (2013.01); *G06T 2207/30004* (2013.01)

(58) Field of Classification Search
CPC ..... A61B 8/085; A61B 8/4245; A61B 8/4263; A61B 8/4461; A61B 8/4472; A61B 8/483; A61B 8/54; A61B 8/58; A61B 8/587; A61N 2005/1058; A61N 2005/1074; A61N 5/1049; A61N 5/1067; G06T 2207/10132; G06T 2207/10136; G06T 2207/30004; G06T 7/251
See application file for complete search history.

(56) References Cited

U.S. PATENT DOCUMENTS

| | | |
|---|---|---|
| 3,987,281 A | 10/1976 | Hodes |
| 3,991,310 A | 11/1976 | Morrison |
| 4,118,631 A | 10/1978 | Froggatt |
| 4,618,978 A | 10/1986 | Cosman |
| 4,882,741 A | 11/1989 | Brown |
| 4,923,459 A | 5/1990 | Nambu |
| 4,943,990 A | 7/1990 | Schar |
| 5,039,867 A | 8/1991 | Nishihara |
| 5,080,100 A | 1/1992 | Trotel |
| 5,086,401 A | 2/1992 | Glassman et al. |
| 5,099,846 A | 3/1992 | Hardy |
| 5,107,839 A | 4/1992 | Houdek et al. |
| 5,117,829 A | 6/1992 | Miller et al. |
| 5,138,647 A | 8/1992 | Nguyen et al. |
| 5,207,223 A | 5/1993 | Adler |
| 5,222,499 A | 6/1993 | Allen et al. |
| 5,233,990 A | 8/1993 | Barnea |
| 5,291,889 A | 3/1994 | Kenet et al. |
| 5,295,483 A | 3/1994 | Nowacki et al. |
| 5,299,288 A | 3/1994 | Glassman et al. |
| 5,301,674 A | 4/1994 | Erikson et al. |
| 5,379,642 A | 1/1995 | Reckwerdt et al. |
| 5,389,101 A | 2/1995 | Heilbrun et al. |
| 5,391,139 A | 2/1995 | Edmundson |
| 5,397,329 A | 3/1995 | Allen |
| 5,408,101 A | 4/1995 | Wong |
| 5,411,026 A * | 5/1995 | Carol .................. A61B 8/08 128/916 |
| 5,438,991 A | 8/1995 | Yu et al. |
| 5,442,675 A | 8/1995 | Swerdloff et al. |
| 5,446,548 A | 8/1995 | Gerig et al. |
| 5,447,154 A | 9/1995 | Cinquin et al. |
| 5,483,961 A | 1/1996 | Kelly et al. |
| 5,511,549 A | 4/1996 | Legg et al. |
| 5,524,627 A | 6/1996 | Passi |
| 5,531,227 A | 7/1996 | Schneider |
| 5,553,618 A | 9/1996 | Suzuki et al. |
| 5,591,983 A | 1/1997 | Yao |
| 5,603,318 A | 2/1997 | Heilbrun et al. |
| 5,609,485 A | 3/1997 | Bergman et al. |
| 5,645,066 A | 7/1997 | Gandini |
| 5,673,300 A | 9/1997 | Reckwerdt et al. |
| 5,690,108 A | 11/1997 | Chakeres |
| 5,715,166 A | 2/1998 | Besl et al. |
| 5,734,384 A | 3/1998 | Yanof et al. |
| 5,740,225 A | 4/1998 | Nabatame |
| 5,754,623 A | 5/1998 | Seki |
| 5,757,881 A | 5/1998 | Hughes |
| 5,778,043 A | 7/1998 | Cosman |
| 5,810,007 A | 9/1998 | Holupka et al. |
| 5,836,954 A | 11/1998 | Heilbrun et al. |
| 5,851,183 A | 12/1998 | Bucholz |
| 5,859,891 A | 1/1999 | Hibbard |
| 5,952,577 A | 9/1999 | Passi |
| 5,991,703 A | 11/1999 | Kase |
| 6,019,724 A | 2/2000 | Gronningsaeter et al. |
| 6,038,283 A | 3/2000 | Carol et al. |
| 6,094,508 A | 7/2000 | Acharya et al. |
| 6,106,470 A | 8/2000 | Geiser et al. |
| 6,112,341 A | 9/2000 | Moreland |
| 6,117,081 A | 9/2000 | Jago et al. |
| 6,119,033 A | 9/2000 | Spigelman et al. |
| 6,122,341 A | 9/2000 | Butler et al. |
| 6,129,670 A | 10/2000 | Burdette et al. |
| 6,144,875 A | 11/2000 | Schweikard et al. |
| 6,146,390 A | 11/2000 | Heilbrun et al. |
| 6,198,957 B1 | 3/2001 | Green |
| 6,208,883 B1 | 3/2001 | Holupka et al. |
| 6,259,943 B1 | 7/2001 | Cosman et al. |
| 6,269,143 B1 | 7/2001 | Tachibana |
| 6,276,211 B1 | 8/2001 | Smith |
| 6,285,805 B1 | 9/2001 | Gueziec |
| 6,292,578 B1 | 9/2001 | Kalvin |
| 6,307,914 B1 | 10/2001 | Kunieda et al. |
| 6,314,310 B1 | 11/2001 | Ben-Haim et al. |
| 6,325,758 B1 | 12/2001 | Carol et al. |
| 6,345,114 B1 | 2/2002 | Mackie et al. |
| 6,359,959 B1 | 3/2002 | Butler et al. |
| 6,366,798 B2 | 4/2002 | Green |
| 6,385,286 B1 | 5/2002 | Fitchard et al. |
| 6,385,288 B1 | 5/2002 | Kanematsu |
| 6,390,982 B1 | 5/2002 | Bova et al. |
| 6,405,072 B1 | 6/2002 | Cosman |
| 6,423,009 B1 | 7/2002 | Downey et al. |
| 6,438,202 B1 | 8/2002 | Olivera et al. |
| 6,459,769 B1 | 10/2002 | Cosman |
| 6,491,702 B2 | 12/2002 | Heilbrun et al. |
| 6,511,430 B1 | 1/2003 | Sherar et al. |
| 6,516,046 B1 | 2/2003 | Fröhlich et al. |
| 6,535,574 B1 | 3/2003 | Collins et al. |
| 6,546,073 B1 | 4/2003 | Lee |
| 6,553,152 B1 | 4/2003 | Miller et al. |
| 6,560,311 B1 | 5/2003 | Shepard et al. |
| 6,567,684 B1 | 5/2003 | Chenevert et al. |
| 6,584,219 B1 * | 6/2003 | Yamashita .............. G06T 15/10 345/422 |
| 6,591,127 B1 | 7/2003 | Mckinnon |
| 6,600,810 B1 | 7/2003 | Hughes |
| 6,621,889 B1 | 9/2003 | Mostafavi |
| 6,628,983 B1 | 9/2003 | Gagnon |
| 6,631,284 B2 | 10/2003 | Nutt et al. |
| 6,636,622 B2 | 10/2003 | Mackie et al. |
| 6,641,539 B2 | 11/2003 | Hirooka et al. |
| 6,661,870 B2 | 12/2003 | Kapatoes et al. |
| 6,662,036 B2 | 12/2003 | Cosman |
| 6,669,635 B2 | 12/2003 | Kessman et al. |
| 6,683,985 B1 | 1/2004 | Kase et al. |
| 6,690,965 B1 | 2/2004 | Riaziat et al. |
| 6,714,627 B1 | 3/2004 | Brown et al. |
| 6,725,079 B2 | 4/2004 | Zuk et al. |
| 6,728,424 B1 | 4/2004 | Zhu et al. |
| 6,731,970 B2 | 5/2004 | Schlossbauer et al. |
| 6,750,873 B1 | 6/2004 | Bernardini et al. |

(56) References Cited

U.S. PATENT DOCUMENTS

| | | | |
|---|---|---|---|
| 6,754,374 B1 | 6/2004 | Miller et al. | |
| 6,785,409 B1 | 8/2004 | Suri | |
| 6,804,548 B2 | 10/2004 | Takahashi et al. | |
| 6,842,502 B2 | 1/2005 | Jaffray et al. | |
| 6,914,959 B2 | 7/2005 | Bailey et al. | |
| 6,915,008 B2 | 7/2005 | Barman et al. | |
| 6,968,224 B2 | 11/2005 | Kessman et al. | |
| 6,980,679 B2 | 12/2005 | Jeung et al. | |
| 7,092,109 B2 | 8/2006 | Satoh et al. | |
| 7,095,823 B2 | 8/2006 | Topolnjak et al. | |
| 7,260,426 B2 | 8/2007 | Schweikard et al. | |
| 7,333,644 B2 | 2/2008 | Jerebko et al. | |
| 7,343,030 B2 | 3/2008 | Sawyer | |
| 7,430,321 B2 | 9/2008 | Okada et al. | |
| 7,438,685 B2 | 10/2008 | Burdette et al. | |
| 7,535,411 B2 | 5/2009 | Falco et al. | |
| 7,613,501 B2 | 11/2009 | Scherch | |
| 7,634,304 B2 | 12/2009 | Falco et al. | |
| 7,662,097 B2 | 2/2010 | Falco et al. | |
| 7,672,705 B2 | 3/2010 | Lachaine et al. | |
| 7,729,744 B2 | 6/2010 | Falco et al. | |
| 7,801,349 B2 | 9/2010 | Wang et al. | |
| 7,824,337 B2 | 11/2010 | Abe et al. | |
| 8,042,209 B2 | 10/2011 | D'souza et al. | |
| 8,057,394 B2 | 11/2011 | Dala-krishna | |
| 8,232,535 B2 | 7/2012 | Olivera et al. | |
| 2001/0035871 A1 | 11/2001 | Bieger et al. | |
| 2001/0049475 A1 | 12/2001 | Bucholz et al. | |
| 2002/0018588 A1 | 2/2002 | Kusch | |
| 2002/0065461 A1 | 5/2002 | Cosman | |
| 2002/0082494 A1 | 6/2002 | Balloni et al. | |
| 2002/0087101 A1 | 7/2002 | Barrick et al. | |
| 2002/0122530 A1 | 9/2002 | Erbel et al. | |
| 2002/0156375 A1 | 10/2002 | Kessman et al. | |
| 2002/0176541 A1 | 11/2002 | Schubert et al. | |
| 2002/0183610 A1 | 12/2002 | Foley et al. | |
| 2002/0188194 A1 | 12/2002 | Cosman | |
| 2003/0018232 A1 | 1/2003 | Elliott et al. | |
| 2003/0028401 A1 | 2/2003 | Kaufman et al. | |
| 2003/0112922 A1 | 6/2003 | Burdette et al. | |
| 2003/0144813 A1 | 7/2003 | Takemoto et al. | |
| 2003/0153825 A1 | 8/2003 | Mooradian et al. | |
| 2003/0182072 A1 | 9/2003 | Satoh et al. | |
| 2003/0231790 A1 | 12/2003 | Bottema | |
| 2004/0015075 A1 | 1/2004 | Kimchy et al. | |
| 2004/0015176 A1 | 1/2004 | Cosman | |
| 2004/0034301 A1 | 2/2004 | Falco | |
| 2004/0092815 A1 | 5/2004 | Schweikard et al. | |
| 2004/0146137 A1 | 7/2004 | Bruder et al. | |
| 2004/0176925 A1 | 9/2004 | Satoh et al. | |
| 2004/0184646 A1 | 9/2004 | Oosawa | |
| 2004/0252870 A1 | 12/2004 | Reeves et al. | |
| 2004/0260142 A1 | 12/2004 | Lovoi et al. | |
| 2005/0010098 A1* | 1/2005 | Frigstad | A61B 5/0002 600/407 |
| 2005/0020917 A1 | 1/2005 | Scherch | |
| 2005/0180544 A1 | 8/2005 | Sauer et al. | |
| 2005/0251029 A1 | 11/2005 | Khamene et al. | |
| 2006/0020195 A1 | 1/2006 | Falco et al. | |
| 2006/0074292 A1* | 4/2006 | Thomson | A61B 6/032 600/411 |
| 2006/0093205 A1 | 5/2006 | Bryll et al. | |
| 2006/0120608 A1 | 6/2006 | Luo et al. | |
| 2006/0241443 A1 | 10/2006 | Whitmore, III et al. | |
| 2006/0285641 A1 | 12/2006 | Scherch | |
| 2006/0293583 A1 | 12/2006 | Saracen et al. | |
| 2007/0015991 A1 | 1/2007 | Fu et al. | |
| 2007/0038058 A1 | 2/2007 | West et al. | |
| 2007/0055090 A1 | 3/2007 | Neustadter et al. | |
| 2007/0167777 A1 | 7/2007 | Abe et al. | |
| 2008/0039713 A1 | 2/2008 | Thomson et al. | |
| 2008/0064953 A1 | 3/2008 | Falco et al. | |
| 2008/0219405 A1 | 9/2008 | Falco et al. | |
| 2008/0292194 A1 | 11/2008 | Schmidt | |
| 2009/0003523 A1 | 1/2009 | Raanes et al. | |
| 2009/0005679 A1* | 1/2009 | Dala-Krishna | A61B 8/0883 600/437 |
| 2009/0093716 A1 | 4/2009 | Deischinger et al. | |
| 2009/0110145 A1 | 4/2009 | Lu et al. | |
| 2009/0226069 A1 | 9/2009 | Razzaque et al. | |
| 2011/0069815 A1 | 3/2011 | Nord et al. | |
| 2011/0172526 A1 | 7/2011 | Lachaine et al. | |

FOREIGN PATENT DOCUMENTS

| | | |
|---|---|---|
| CA | 2768515 A1 | 7/2011 |
| CA | 2768515 C | 7/2017 |
| DE | 102008030244 A1 | 12/2009 |
| EP | 0647457 A1 | 4/1995 |
| EP | 951697 A1 | 10/1999 |
| EP | 1304960 A1 | 5/2003 |
| EP | 1426806 A2 | 6/2004 |
| EP | 1757228 A1 | 2/2007 |
| EP | 2523623 B1 | 10/2018 |
| FR | 2778574 A1 | 11/1999 |
| JP | 2006000220 A | 1/2006 |
| WO | WO-9902074 A1 | 1/1999 |
| WO | WO-9906644 A1 | 2/1999 |
| WO | WO-9926534 A1 | 6/1999 |
| WO | WO-9927839 A2 | 6/1999 |
| WO | WO-2001005316 A1 | 1/2001 |
| WO | WO-0209588 A1 | 2/2002 |
| WO | WO-2002009588 A1 | 2/2002 |
| WO | WO-03076003 A2 | 9/2003 |
| WO | WO-2003076003 A2 | 9/2003 |
| WO | WO-2006051523 A2 | 5/2006 |
| WO | WO-2009053896 A2 | 4/2009 |
| WO | WO-2011085469 A1 | 7/2011 |

OTHER PUBLICATIONS

"U.S. Appl. No. 12/956,991, Final Office Action dated Nov. 5, 2014", 20 pgs.

"U.S. Appl. No. 12/956,991, Non Final Office Action dated Apr. 16, 2014", 15 pgs.

"U.S. Appl. No. 12/956,991, Response filed Mar. 4, 2015 to Final Office Action dated Nov. 5, 2014", 18 pgs.

"U.S. Appl. No. 12/956,991, Response filed Jul. 16, 2014 to Non Final Office Action dated Apr. 16, 2014", 25 pgs.

"U.S. Appl. No. 12/956,991, Response filed Nov. 26, 2013 to Restriction Requirement dated Aug. 26, 2013", 11 pgs.

"U.S. Appl. No. 12/956,991, Restriction Requirement dated Aug. 26, 2013", 9 pgs.

U.S. Appl. No. 12/956,991, filed Nov. 30, 2010, Feature Tracking Using Ultrasound.

"International Application Serial No. PCT/CA2010/002008, Written Opinion dated Mar. 14, 2011", 3 pgs.

"Claim Chart for Claim 10 of U.S. Pat. No. 5,447,154", (Jan. 12, 2006), 3 pgs.

"Conformal Radiation Therapy", UCSF [Online]. Retrieved from the Internet: <http://www.ucsf.edu/ipouliot/Course/conformal_radiation_therapy.htm>, (Accessed on Sep. 16, 2004), 3 pgs.

"IMRT Technology & Program", Emory radiation oncology, [Online]. Retrieved from the Internet: <http://www.emoryradiationoncology.org/high-technology.htm>, (Accessed on Sep. 14, 2004), 1 pg.

"Varian's Smartbeam IMRT Intensity Modulated Radiation Therapy", Varian Medical Systems, [Online]. Retrieved from the Internet: <http://www.varian.com/pinf/imr000c.html>, (Accessed Sep. 14, 2004), 2 pgs.

Benedict, Stanley H, "Looking Into Patient Positioning and Organ Motion", VCO Heath System, [Online]. Retrieved from the Internet: <http://www.acmp.org/meetings/hershey_2001/highlights/benedict.pdf> via Wayback Machine, (Accessed on Feb. 10, 2006), 11 pgs.

Boctor, et al., "A Rapid Calibration Method for Registration and 3D Tracking of Ultrasound Images Using Spatial Localizer", Proceedings of the SPIE, (2003), 12 pgs.

Boyer, A, "A review of electronic portal imaging devices (EPIDs)", Med. Phys. 19 (1), (1992), 16 pgs.

(56) References Cited

OTHER PUBLICATIONS

Cuisenaire, O, et al., "Automatic retrospective methods", [Online]. Retrieved from the Internet: <http//www.tele.ucl.ac.be/PEOPLE/OC/these/node75.html>, (Aug. 10, 2004), 1 pg.

Cuisenaire, O, et al., "Chamfering", [Online]. Retrieved from the Internet: <http//www.tele.ucl.ac.be/PEOPLE/OC/these/node12.html>, (Aug. 10, 2004), 4 pgs.

Cuisenaire, O, et al., "Manual Retrospective methods", [Online]. Retrieved from the Internet: <http//www.tele.ucl.ac.be/PEOPLE/OC/these/node74.html>, (Aug. 10, 2004), 1 pg.

Hanks, et al., "Three Dimensional Conformal External Beam Treatment of Prostate Cancer", [Online]. Retrieved from the Internet: <http://prostate-help.org/download/pilgrim/10rad.pdf>, (1997), 3 pgs.

Krempien, et al., "Daily patient set-up control in radiation therapy by coded light projection", (2002), 3 pgs.

Le Verre, C, et al., "Intensity-Based Registration of Portal Images for Patient Positioning in Radiotherapy", Grenoble cedex 09 • France, (2009), 9 pgs.

Leszczynski, K W, et al., "An Image Registration scheme applied to verification of radiation therapy", British Journal of Radiology British Inst. Radial UK, [Online]. Retrieved from the Internet: <http://bjr.birjournals.org/cgi/reprinU71/844/413.pdf>, (Apr. 1998), 14 pgs.

Michalski, et al., "Three-Dimensional Conformal Radiation Therapy (3DCRT) for Prostate Cancer", Radiation Oncology Center, Mallinckrodt Institute of Radiology, Washington University Medical Center, St. Louis, Missouri, (1996), 8 pgs.

Pollack, et al., "Conventional vs. Conformal Radiotherapy for Prostate Cancer: Preliminary Results of Dosimetry and Acute Toxicity", Int. J. Radiation Oncology Biol. Phys., 34(3), (1996), 555-564.

Reinstein, L, et al., "Radiotherapy Portal Imaging Quality, Report of AAPM Task Group No. 28", American Association of Physicists in Medicine by the American Institute of Physics, New York, (1988), 30 pgs.

Thayananthan, A, et al., "Shape Context and Chamfer Matching in Cluttered Scenes", [Online]. Retrieved from the Internet: <http://mi.eng.cam.ac.uk/~bdrs2/papers/thayananthan cvpr03.pdf>, (Aug. 10, 2004), 1-8.

"Canadian Application Serial No. 2,768,515, Examiner's Rule 30(2) Requisition dated Jul. 26, 2016", 3 pgs.

"Canadian Application Serial No. 2,768,515, Response filed Oct. 17, 2016 to Examiner's Rule 30(2) Requisition dated Jul. 26, 2016", 17 pgs.

"European Application Serial No. 10842792.3, Communication pursuant to Article 94(3) EPC dated Oct. 10, 2016", 6 pgs.

"European Application Serial No. 10842792.3, Office Action dated Apr. 11, 2018", 6 pgs.

"European Application Serial No. 10842792.3, Response filed Apr. 20, 2017 to Communication pursuant to Article 94(3) EPC dated Oct. 10, 2016", 19 pgs.

"European Application Serial No. 10842792.3, Response filed Oct. 5, 2015 to Extended European Search Report dated Mar. 5, 2015", 10 pgs.

"Gemedicalsystems", [Online]. Retrieved from the Internet: http://www.gehealthcare.com/cgi-bin/print/print.cgi, (Accessed on Sep. 14, 2004), 2 pgs.

Booth, "Modelling, the impact of treatment uncertainties in radiotherapy", University of Adelaide, [Online]. Retrieved from the Internet: <http://thesis.library.adelaide.edu.au/uoloads/approved/adt-SUA20020816.175301/public/03chapter2.pdf>, (Mar. 2002), 244 pgs.

\* cited by examiner

FEATURE TRACKING USING ULTRASOUND

CROSS-REFERENCES TO RELATED APPLICATIONS

This application is a continuation of U.S. Ser. No. 12/956,991, filed Nov. 30, 2010, which claims priority to and the benefit of U.S. provisional patent application Ser. No. 61/294,294, filed Jan. 12, 2010, and U.S. provisional patent application Ser. No. 61/323,064, filed Apr. 12, 2010, each entitled "Feature Tracking Using Ultrasound."

TECHNICAL FIELD

This invention relates to methods for tracking features during a medical procedure.

BACKGROUND INFORMATION

One purpose of radiotherapy is to target a specified anatomical region suspected of having either gross or suspected microscopic disease (sometimes referred to as the clinical treatment volume, or "CTV") with radiation while sparing surrounding healthy tissues and at-risk organs. Typically, a physician outlines the CTV on one or more planning images, such as a computed tomography (CT) image, magnetic resonance (MRI) image, three-dimensional ultrasound (3DUS) image, or a positron emission tomography (PET) scan. A treatment plan is then developed which optimizes the radiation dose distribution on the planning images to best accomplish the prescribed goals. The plan may be based on certain treatment parameters such as beam directions, beam apertures, dose levels, energy and/or type of radiation. The treatment is generally given in a finite number of fractions, typically delivered once a day. During treatment, the patient is positioned relative to the radiation beam prior to each fraction according to the treatment plan.

In practice, a margin is included around the CTV to account for anatomical changes in the CTV and surrounding areas. These changes can result from either interfractional motion, i.e., anatomical differences that develop immediately prior to the current fraction (often due to an inaccurate set-up or actual organ motion such as a different state of bladder fill), or from intrafractional motion, i.e., anatomical motion which occurs during the actual treatment delivery. In some instances, both types of motion may be present. In some instances, intrafractional motion may be cyclical, as caused by breathing, or random, as caused by gas or a steadily increasing bladder volume.

Some conventional image-guided radiotherapy (IGRT) applications may be used to track interfractional motion. Various imaging modalities may be used to implement IGRT, including three-dimensional ultrasound (3DUS) and x-ray imaging of fiducial "seeds" implanted in a patient's organ. Image capture is typically performed once prior to the radiation delivery, and the treatment couch is then adjusted to compensate for any changes in anatomy relative to the treatment plan. The use of IGRT to account for intrafractional motion, on the other hand, is in its infancy and requires continuous imaging throughout the treatment. As trends in radiotherapy begin to move towards fewer fractions and longer treatment times, correcting for intrafractional motion is growing in importance.

One method of tracking intrafractional motion uses x-rays to image fiducials at discrete points in time throughout treatment. However, continuous monitoring is not achievable with this methodology because the x-ray imaging exposure is unbearably high, with an image frequency of 30 seconds being the currently acceptable limit. Such procedures still require undesirable extra radiation as well as an invasive fiducial implantation procedure. Further, various surface monitoring technologies have been developed for cyclical intrafractional motion, but these do not provide internal information and are not sufficient in many applications, particularly when random motion occurs. Yet another technology uses beacons which are implanted in the feature of interest, and tracked in real-time using electromagnetic methods. As with fiducials, this procedure also requires an invasive implantation procedure.

Two-dimensional ultrasound (2DUS) can conceivably be proposed for intrafractional motion detection as it is real-time in nature, does not add radiation exposure to the patient during the monitoring process, and does not require implantation of fiducials. Temporally-spaced 2DUS images, as well as three-dimensional ultrasound (3DUS) images, have been proposed to track intrafractional motion during radiotherapy. See, for example, Xu et al, Med. Phys. 33 (2006), Hsu et al, Med. Phys. 32 (2005), Whitmore et al, US 2006/0241143 A1, Fu et al, US 2007/0015991 A1, and Bova et al, U.S. Pat. No. 6,390,982 B1. Some of these disclosures discuss the use of 3DUS probes to obtain a "four-dimensional" image series, however, there remain many obstacles in obtaining and using these images which are not addressed in the current literature.

One conventional three-dimensional (3D) probe utilizes a motorized two-dimensional (2D) probe placed inside a housing that sweeps mechanically within the housing, thus collecting a series of two-dimensional slices to cover the three-dimensional volume. For example, imaging a 10 cm×10 cm area at a given depth using a resolution of 0.5 mm, each sweep requires 200 slices. At a frame rate of 20 Hz, one sweep takes approximately 10 seconds to complete, which precludes effective "real-time" four-dimensional imaging (three physical dimensions changing over time). Moreover, reconstruction of the entire three-dimensional volume takes at least two seconds which further reduces the theoretical three-dimensional refresh rate to 12 seconds, although multi-thread processing may help. Anatomical feature extraction based on the three-dimensional images is also time consuming and requires at least an additional five seconds. Aspects of this invention allow for real-time feature tracking ultrasound imaging during a medical procedure.

SUMMARY OF THE INVENTION

Various implementations of the invention provide techniques and supporting systems that facilitate real-time or near-real-time ultrasound tracking for the purpose of calculating changes in anatomical features during a medical procedure. While the methods are primarily described in terms of a radiotherapy fraction, other applications are contemplated, such as cryotherapy, brachytherapy, high-intensity focused ultrasound (HIFU), as well as imaging procedures such as computed tomography (CT), four-dimensional CT, planar x-ray, PET, MRI, and SPECT, or any other medical procedure where it is important to monitor anatomical features throughout the treatment.

Although primarily concerned with intrafractional motion tracking, in some cases correction for interfractional motion may also be implemented prior to the tracking process. In some cases, a hybrid technique of acquiring a temporally-spaced combination of three-dimensional ultrasound images and targeted subsets of two-dimensional ultrasound images may be used. The two-dimensional ultrasound images are used to increase the frequency of feature tracking to render the process as close to real-time as possible.

In a first aspect, a computer-implemented method for tracking an anatomical feature or features (e.g., an organ, tumor, tumor bed, gland, critical anatomical structure, or other lesion) within a patient undergoing a medical procedure such as radiotherapy, radiotherapy planning, image-guided surgery, or other treatment includes obtaining a three dimensional image of a region that includes the feature being treated and determining the location of the feature within the region. The three dimensional image is obtained at a first periodicity (e.g., every 30 seconds) as to reduce the processing and storage burdens as compared to higher frequencies. In between each three dimensional image, a series of temporally-displaced targeted subsets of ultrasound images focused on the region are obtained at a greater periodicity (e.g., every 0.1-3 seconds), and each is compared with the three dimensional image to determine if there has been any changes to the feature (e.g., movement, morphing). To reduce processing and memory requirements, the targeted subsets are typically of lower quality, resolution and/or represent a smaller area of the region than that of the three dimensional images, thereby allowing for more frequent imaging and comparisons. In some preferred embodiments the target subsets are planes of ultrasound data rather than a full reconstructed 3D volume.

In some cases, a determination is made as to whether the displacement exceeds a displacement threshold (such as an upper limit of spatial displacement of the feature of interest) and if so, an updated three dimensional image of the region of interest is obtained sooner than would be obtained according to the first periodicity. The updated three dimensional image maybe used for subsequent comparisons with the targeted set of ultrasound images. In addition (or alternatively) a determination is made as to whether the displacement exceeds a safety threshold and if so, the medical procedure is halted to allow for one or more adjustments to the patient's orientation with respect to a treatment device. In certain implementations, one or more treatment apparatus (e.g., a treatment couch on which the patient is supported and/or a multi-leaf collimator for administering radiation therapy) may be continuously adjusted while treatment is being delivered to compensate for the displacement.

In some embodiments, image parameters used in obtaining the targeted subset of ultrasound images are adjusted based on the displacement. The displacement threshold may be an upper limit on spatial displacement of the feature or exceeding some predefined change in size. The comparison may, in some cases, include comparing grey-scale values of subsequent images to determine the displacement or shift of the feature.

The targeted subset may be a series of two dimensional image slices of the feature, a combination of two or more tracking planes (such as two orthogonal planes), which may, in some cases, be reconstructed as a set of voxels intersecting the planes. The images may be used as obtained, or, in some cases segmented. The images may be obtained from various angles and directions aimed at the feature, including, for example transperineally in the case of a prostate gland. In certain implementations, the targeted subset may be three dimensional ultrasound datasets related to a limited region of interest, which may be determined on an adjusted sector size, an adjusted image depth and/or an adjusted ultrasound sector angle and in some cases have a reduced resolution.

The three dimensional ultrasound images may be obtained using a motorized probe, a bi-planar probe or a matrix probe, any of which may be internal or external to the patient. In some instances, the probe may have traceable markers attached to it and be calibrated to pixels within the images to facilitate spatial tracking over time with respect to a particular coordinate system.

The feature to be tracked can be the target lesion being treated, a subset of the lesion, another feature which is proximal to the lesion, a fiducial, or any other feature deemed to be of importance during the medical procedure. Features may be extracted from both full three-dimensional ultrasound images as well as the targeted subset of ultrasound images to obtain a representation of the feature's motion in time, using either segmentation or pattern recognition algorithms.

In another aspect, a system for tracking an anatomical feature within a patient undergoing a medical procedure includes a processor and a memory register. The processor is configured to locate the feature of interest within a series of three dimensional images and iteratively compare temporally displaced targeted subsets of ultrasound images obtained at a periodicity greater than the first periodicity with the three dimensional image. The processor then determines, based on each comparison, a displacement of the feature of interest. The register receives and stores the images.

In some versions, the processor determines if the displacement exceeds a displacement threshold (an upper limit of spatial displacement of the feature of interest, for example) and if so, provide instructions to obtain an updated three dimensional image of the region of interest sooner than would be obtained based on the first periodicity. The processor may also determine if the displacement exceeds a safety threshold. If so, the processor can provide instructions to halt the medical procedure, thereby allowing for adjustments to be made to the patient's orientation with respect to a treatment device and/or to the orientation of the treatment device itself prior to reinstating the procedure.

In some cases, the system also includes an ultrasound probe for providing the images to the register. The probe may be a two dimensional ultrasound probe rotatably mounted into a housing such that the probe can move according to at least one degree of freedom, either longitudinally, in a sweeping motion about an axis or rotating about an axis. A motor may provide movement to the probe, based, for example, on instructions from a controller to alter the position of the probe relative to the patient, the housing or both. The controller may also provide additional adjustments to one or more imaging parameters. Some embodiments may also provide a display and/or input devices, thus allowing an operator to view the images and interact with the system.

Changes identified in the feature may trigger a warning message (either visual, textual, audio or some combination thereof), warning the operator that the medical procedure should be modified. In other implementations, the changes may cause continuous or semi-continuous modifications to the treatment as it progresses.

BRIEF DESCRIPTION OF FIGURES

In the drawings, like reference characters generally refer to the same parts throughout the different views. Also, the drawings are not necessarily to scale, emphasis instead generally being placed upon illustrating the principles of the invention.

DETAILED DESCRIPTION

Throughout the following descriptions and examples, aspects and embodiments of the invention are described in the context of tracking intrafractional motion during the delivery of radiotherapy. However, it is to be understood that the present invention may be applied to tracking attributes of virtually any feature within or on a patient during any form of medical procedure requiring anatomical tracking, such as external beam and brachytherapy, cryotherapy, hyperthermia, high intensity focused ultrasound treatments (HIFU)) and/or various forms of imaging (e.g., CT, 4DCT, PET, US, SPECT, and MRI).

Figure 1:
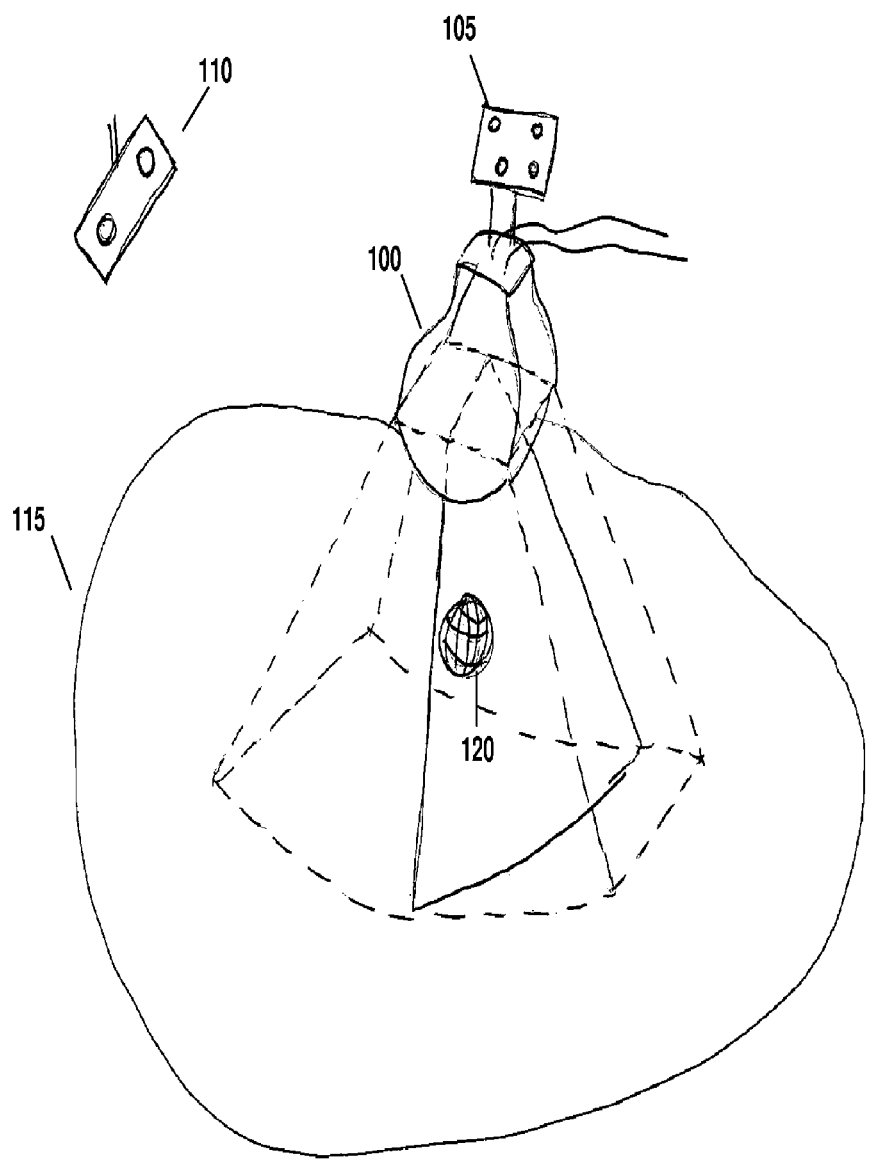
FIG. 1 is a schematic diagram illustrating the use of a mechanical three-dimensional probe, referenced to a room coordinate system, for imaging a feature within a patient according to various embodiments of the invention.

Referring to FIG. 1, a motorized, mechanically sweeping three-dimensional ultrasound probe 100, which is of particular use in this application, contains a two-dimensional probe inside of a housing, the two-dimensional probe being able to sweep at different angles within the housing, controlled by a motor. In certain applications, tracking markers 105 are affixed to the probe handle such that the position of the probe can be detected by a tracking system 110. One such tracking device utilizes an infrared optical camera, which tracks infrared signals emitted from or reflected by the markers. The position and orientation of the probe housing can therefore be determined at all times, based on a relative coordinate system. In certain applications, the individual ultrasound pixels are referenced to a coordinate system useful for the medical procedure, which can for example be tied to room, a treatment device, an imaging device, or a patient.

Because the motorized sweeping probe is essentially a two-dimensional probe that moves according to a particular degree of freedom inside the housing, its position within the housing can be quantified in terms of a parameter X. The parameter X can be measured as an angle in the case of rotational sweep inside the housing, or as a distance in the case of a linear sweep. The parameter X can be controlled by a controller though an interface to the motor. For example, the controller may instruct the motor to move the two-dimensional probe to a particular location within the housing such that a two-dimensional frame can be acquired at a fixed position X. In other cases, the controller may instruct the motor to continuously move probe within the housing, facilitating the acquisition of a three-dimensional sweep by acquiring a series of temporally-displaced image frames while continuously changing X.

In some applications, pixels in a given two-dimensional frame at position X are known relative to a fixed room coordinate system. One method of attributing coordinates to the pixels is to use a calibration algorithm similar to those developed for freehand 3DUS imaging, but using a fixed $X=X_{cal}$, which relates all pixels in a "calibration slice" to the probe markers and hence to the room coordinate system. Known geometry of the three-dimensional probe can then be used to relate this calibration to the slices with other X values.

Calibration may also be achieved by temporarily affixing the three-dimensional probe to a phantom having embedded geometrical features. In such cases, a CT scan of the probe and phantom assembly is acquired, and then a three-dimensional sweep is acquired with the probe still fixed relative to the phantom. The 3DUS images are aligned relative to the CT scan using software that allows rotations and translations of the images such that the geometrical features visible in the 3DUS images match those as seen on CT. In some cases, segmented features extracted from the CT may be used instead of the CT pixel values themselves. The markers affixed to the probe handle are also visible on CT, and thus a relationship between the 3DUS pixels and the markers can be quantified, thus allowing each 3DUS pixel to be known relative to the markers. The pixels can then be referred back to the room coordinate system using known techniques used in the art for freehand 3DUS imaging.

For intrafractional tracking of a structure or anatomical feature, the probe is placed on the patient 115 prior to treatment such that the target 120 is within the field of view of the probe. The technique may be used, for example, for transperineal imaging of the prostate, or imaging of a breast tumor. A full three-dimensional image of the target structure 120 and its surrounding anatomy is acquired by continuously varying X, during which the ultrasound images are acquired at a given frame-rate f. The frame-rate is primarily limited by ultrasound physics such as the time needed to send and receive a sound wave, but also may be limited by hardware and computer processing constraints. A typical frame-rate is on the order of 20 Hz. As described above, the pixels in each frame at a known X can be attributed to certain coordinates in the room coordinate system, and therefore the two-dimensional slices can be used to a "reconstructed" 3DUS volume in reference to the room coordinate system.

Prior to radiotherapy, the patient is typically placed on the treatment table according to skin markings. Correction for interfractional motion can then be performed by imaging of the target or a proximal feature and adjusting the patient's position relative to the room coordinate system either by moving the patient, the couch, or both. This corrects for daily setup errors as well as changes in the anatomy since the treatment planning phase, and can be done with any number of known IGRT techniques. In some cases, this process may be accomplished by acquiring a first three-dimensional sweep of the target structure with the mechanized probe. Typically, the patient couch is moved to correct for initial target misalignments, although other strategies can be used such as modifying the treatment plan. However, this initial interfractional correction does not account for motion during the treatment itself (intrafractional motion), as addressed below.

After initial patient setup, successive temporally-displaced three-dimensional sweeps of the target structure, or more generally of anatomical features related to or near the target structure or other area of interest, can be acquired using the mechanized probe. Displacement of the feature or features in each successive image relative to previous images can then be determined. In one method, a difference in the grayscale between the images is quantified, or, in other cases, a segmentation algorithm is used to recontour the features in each image and the displacement between successive segmentations is determined. One or more treatment parameters may then be modified as the feature changes location or form. These modifications can be, but are not limited to: warning the operator that the feature has moved outside a given tolerance and instructing her to halt treatment and reposition the patient; automatically halting the treatment beam by synchronizing with the linear accelerator if the feature moves past a given tolerance; correcting for the displacement by automatically adjusting the couch, and then turning on the beam again; iteratively adjusting the beam (for example, by moving the couch, the beam, or both) as the linear accelerator is turned off and on; and/or continuously changing the beam shapes or alignment in synchrony with newly updated feature positions. In some cases, no modification is instituted if the feature has not changed or the changes are within allowable tolerances.

Although successive acquisition of three-dimensional images may be useful, the images are not truly real-time because of the time delay inherent in the "sweep" process. More specifically, the sweeping technique includes varying X during the sweep to acquire enough frames for reconstruction without gaps between the frames, which is limited by the frame-rate of the ultrasound (which itself is limited by ultrasound physics), creating a full three-dimensional reconstruction of the two-dimensional slices into a full three-dimensional ultrasound volume, and calculation of a representation of the feature from the images.

Strategy 1: Hybrid three-dimensional and two-dimensional temporal tracking.

Figure 2:
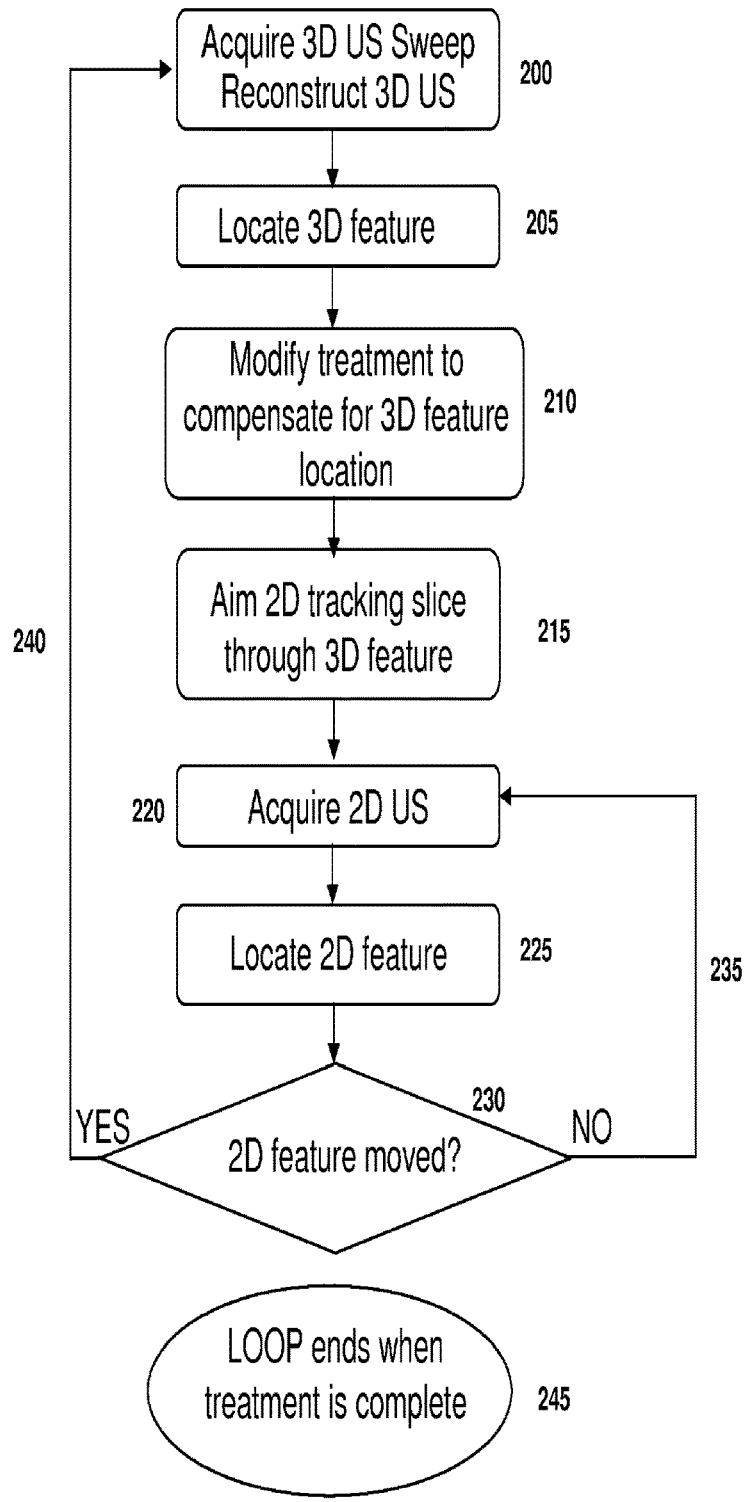
FIG. 2 is a flow-chart illustrating a method for implementing a hybrid three-dimensional and two-dimensional temporal tracking strategy according to various embodiments of the invention.

One approach to using ultrasound for real-time treatment monitoring uses targeted subsets of three-dimensional ultrasound images ("TUS"), and is illustrated in FIG. 2. In step 200, a full three-dimensional sweep of the patient's anatomy, including the feature to be tracked, is acquired by continuously (or in many small discrete steps) varying X to acquire a full set of two-dimensional slices. The two-dimensional slices are then reconstructed in the room coordinate system, using each tagged X-position of the slices as well as the tracking camera information and calibration information, to form a 3DUS image.

In step 205, the three-dimensional feature is located in the 3DUS image. This feature is referred to herein as the three-dimensional feature, as it is determined from a three-dimensional image, as opposed to a feature in a two-dimensional slice image, which is referred to as a two-dimensional feature. The location can be determined manually, semi-automatically, or fully automatically. For example, a three-dimensional pattern recognition algorithm may be used, or in the case of imaging a prostate, the user can place one or more "hint points" (i.e., one point in the center or 4-8 points on the prostate edges), to initiate a segmentation algorithm which then determines the full prostate surface in three dimensions. Alternatively, a contour from a planning session can be superimposed onto the three-dimensional image as an initial guess, and potentially warped to better fit the edges in the current image.

In step 210, the treatment is modified to account for the current position of the feature as found in step 205. This can be accomplished, for example, by moving the couch to align the feature (either manually or automatically) if the feature does not significantly change volume or shape. The beam may be temporarily stopped in some cases to allow for the couch motion. Other strategies may include completely recalculating the treatment plan, or re-shaping the beam apertures to better target the feature.

In step 215, the X-position of the motorized probe is moved to a fixed position such that the two-dimensional ultrasound slice is optimally aimed at the feature. For example, if the feature is an organ such as the prostate or a breast lumpectomy cavity, which has been segmented, the beam can be aimed at the center of the structure. The optimal slice can alternatively be selected based on feature discernibility statistics extracted from the three-dimensional image at step 205. In step 220, a two-dimensional ultrasound slice is acquired at this fixed X-position, which is targeted at the feature, and in step 225 the two-dimensional feature is located in this ultrasound slice. In step 230, if size, shape and/or locational characteristics of the feature have not changed since step 205, another two-dimensional acquisition and feature location is executed (step 235). The process is then repeated until changes in the two-dimensional feature are identified.

A change may include, for example, that the feature has moved outside of the two-dimensional plane, which would result in a significant change in the grayscale values in the region of interest surrounding the feature. The change may also be due to movement of the feature within the two-dimensional plane by an amount greater than a pre-determined threshold, or that the feature has changed shape greater than a predetermined threshold. For prostate imaging, the two-dimensional plane is typically aligned with the sagittal plane which can detect anterior/posterior and superior/inferior motions, which are the most common, with left-to-right motions being much less common. An acceptable threshold may be 2 mm, meaning so long as the prostate center moves by less than 2 mm, step 235 is continued. If the displacement is greater than 2 mm (or some other threshold), the process moves to step 240. Another reason to transition to step 240 is if that the two-dimensional prostate area changes significantly from one frame to the next, which implies that the prostate has moved out-of-plane—either to the right or left. In some applications, the location, alignment and/or orientation of the probe may be altered by a robotic arm into which the probe is placed.

At step 240, a new full 3DUS sweep is initiated, and the process is repeated. The entire flowchart loop is continued until the treatment is completed. Using this methodology, three-dimensional acquisition is triggered if motion is detected based on two-dimensional image acquisitions, which, due to the lower processing demands, allows for real-time monitoring. As such, a full three-dimensional adaptation of the treatment is triggered only if it appears that the feature has moved out of tolerance. In some embodiments, step 240 is initiated not only if the feature has likely moved out of tolerance, but also at regular temporal intervals (e.g., every fifteen seconds) as an extra check.

This approach may be used in applications when movement has a high likelihood to be in a particular two-dimensional plane chosen by the orientation of the motorized probe. In some variations, when this likelihood is high, modification of the treatment can be added as a step between 225 and 230 such that the two-dimensional tracking info is used to identify treatment modifications in real-time.

Strategy 2: Hybrid three-dimensional and multiple two-dimensional plane temporal tracking.

Figure 3:
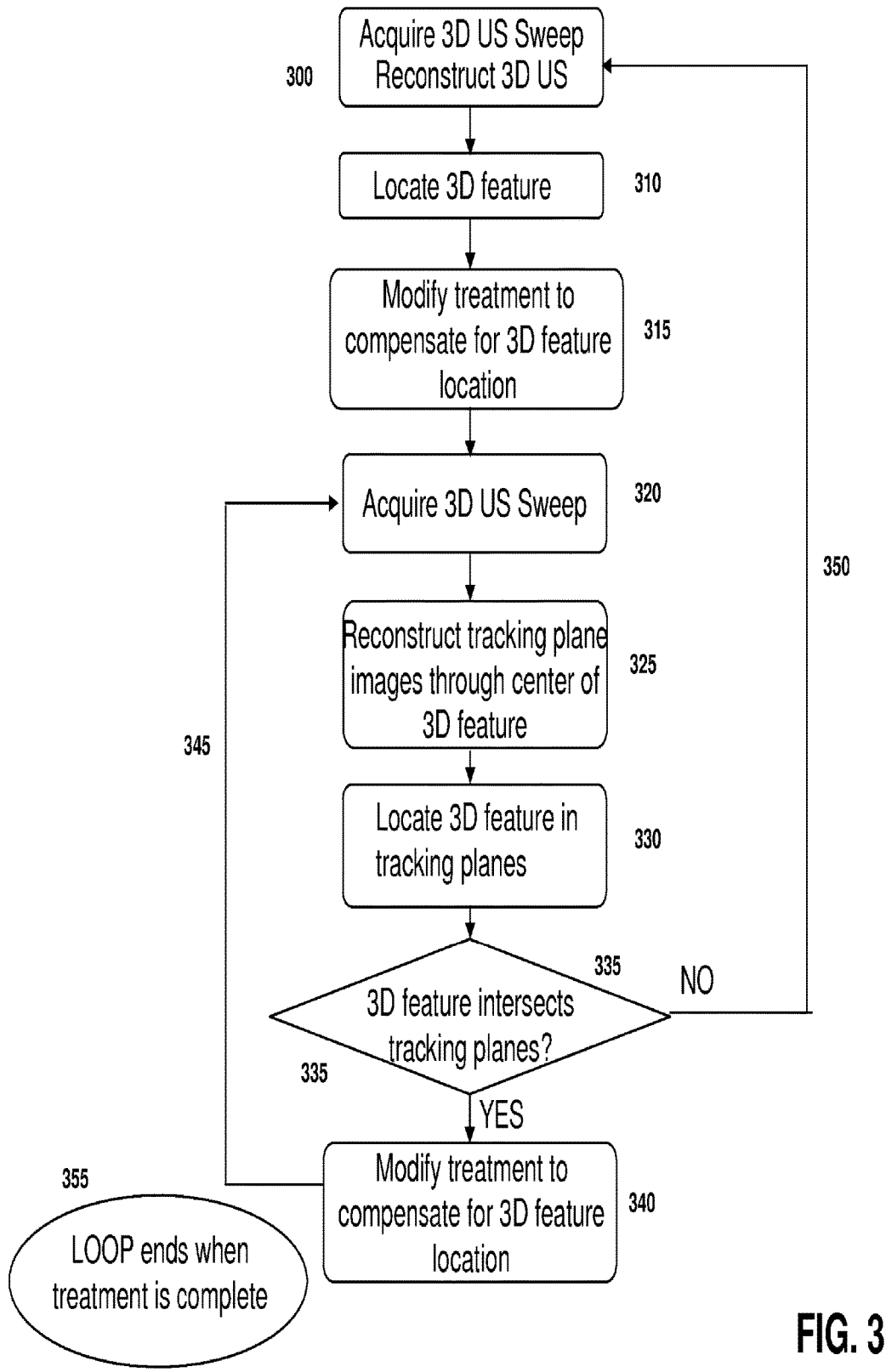
FIG. 3 is a flow-chart illustrating a particular implementation of a hybrid three-dimensional and multiple two-dimensional plane temporal tracking strategy according to various embodiments of the invention.
Figure 4:
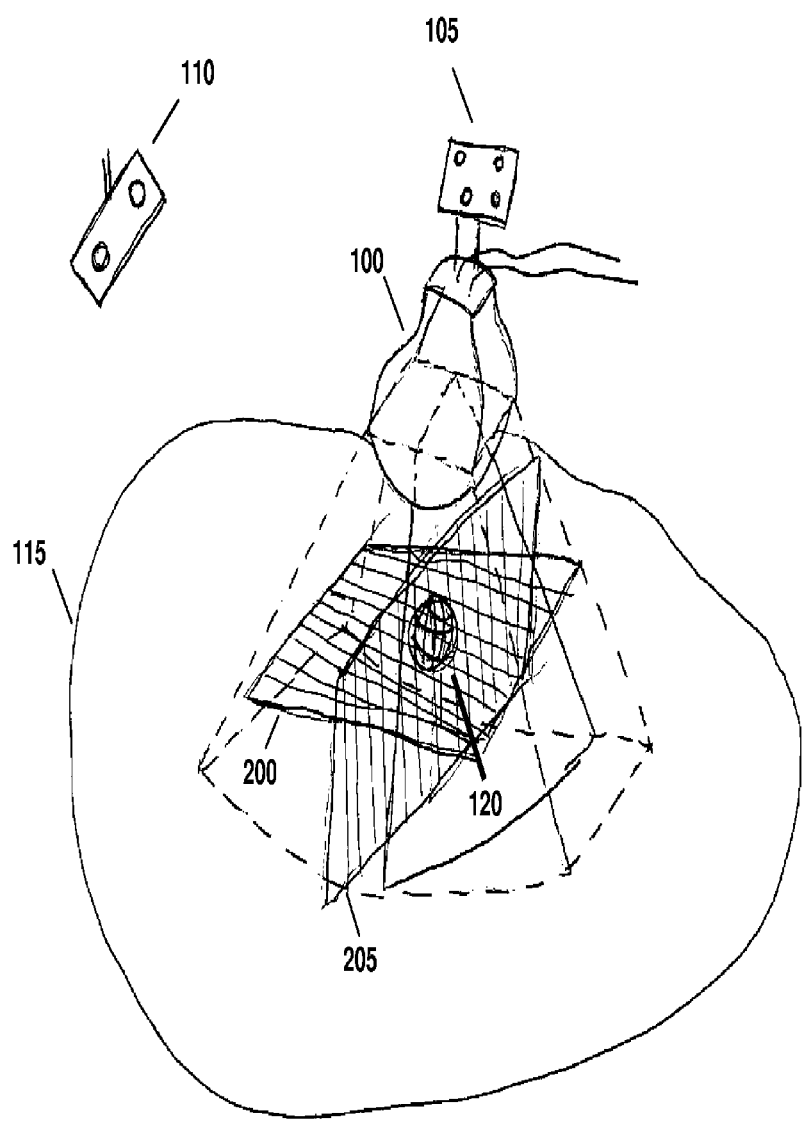
FIG. 4 illustrates the use of tracking planes in the method of FIGS. 2 and 3.

In some applications in which the motion is not likely to be primarily constrained to a particular two-dimensional plane, a hybrid of three-dimensional and multiple two-dimensional plane temporal tracking techniques may be used. Referring to FIG. 3, steps 300, 310 and 315 are the same as 200, 210 and 215 of FIG. 2, respectively. In step 320, a full sweep is acquired by the motorized probe. In step 325, instead of reconstructing the entire three-dimensional image set, only the pixels in two or more tracking planes, preferably being orthogonal or close to orthogonal to each other, are reconstructed. An example is shown in FIG. 4, showing tracking planes 200 and 205 being used for reconstruction.

The planes are selected so as to intersect with the feature 120. In the case of an organ such as the prostate, the planes preferably intersect through the center of the organ, which can be found from computing the centroid of the segmented structure. As used herein, "reconstructed ultrasound plane" refers to a reconstruction of a voxel set attached to a single plane, as opposed to a complete three-dimensional reconstruction that reconstructs the entire 3D voxel set. While limiting the information available to only certain planes, the computational requirements to produce only the reconstructed ultrasound plane(s) are significantly lower. As such, step 325 saves time and memory space, since it is much quicker and more efficient to reconstruct pixels in planes than an entire voxel space, as well as locate changes in features, thus reducing temporal intervals between successive localizations. In some cases, one of the tracking planes is not a reconstructed plane, but consists of the pixels from an actual two-dimensional ultrasound image from a fixed position (at one particular X location) of the motorized probe, as described above in reference to FIG. 2.

Figure 3A:
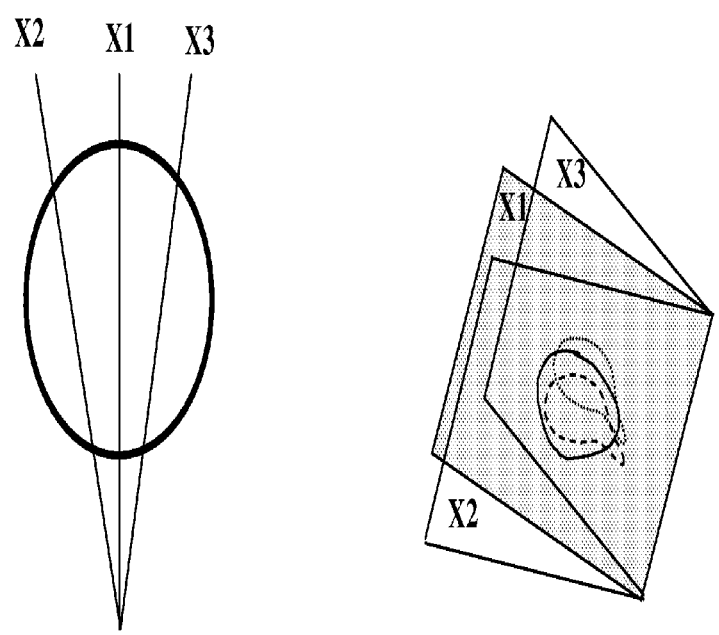
FIG. 3A illustrates a particular implementation of a hybrid three-dimensional and multiple two-dimensional plane temporal tracking technique according to various embodiments of the invention.

In other applications, none of the tracking planes are reconstructed, but consist of pixels from multiple two-dimensional ultrasound images obtained from different positions of the motorized probe along the X plane. For example, as shown in FIG. 3A, three plane positions can be selected, at positions $X_1$ (in the center of the feature), $X_2$ (to the left of center but still imaging part of the feature) and $X_3$, (to the right of center but still imaging part of the feature). The probe can then obtain images at each of these positions in rapid succession in any convenient order without need for reconstruction. The X positions relative to the center of the feature can be strategically determined based, for example, on knowledge of the three-dimensional surface of the feature.

Referring back to FIG. 3, in step 330, the three-dimensional feature is located in the tracking planes, creating a three-dimensional surface, that when intersected by a plane, produces a two-dimensional curve. In one method, the shape and volume of the three-dimensional feature, as found in the first iteration of step 310, is assumed to remain constant. By determining where the two-dimensional curves generated by cutting through the tracking planes best fit the grayscale values yields the desired three-dimensional location of the surface, and thus displacement of the feature relative to its position at the previous point in time. "Best fit" can mean, for example, maximization of the sum of image gradients along the curves.

Finding the location of the three-dimensional feature from the tracking planes assumes that at least part of the feature is visible in at least two planes, and increasing the number of planes (e.g., from two to three, or even higher), increases the likelihood that the feature is visible. In some cases, the feature may move to a position where it is no longer visible, as determined at step 335. This determination can be made based on a failure of the process at step 330, for example. If, however, the feature remains visible in one or more of the planes, the treatment is modified to account for the new position (step 340) and acquisition of tracking plane data continues (step 345) to make further adjustments. The position of the tracking planes in 325 may be re-centered to account for the displaced feature found in 330. In the case where feature is no longer in the planes, the full 3DUS volume is reconstructed (step 350). This allows for re-centering of the tracking planes for further iterations, and to ensure that the tracking planes intersect the feature being tracked. The process illustrated in FIG. 3 ends once the treatment is complete (step 355). In some variations, path 350 will be taken even if the feature is still intersected by the tracking planes, at fixed time intervals in order to gather full three-dimensional data at various points in time.

Using this approach, the full three-dimensional displacement can be calculated as long the tracking planes intersect with the feature, thus reducing the number of times the full three-dimensional image needs to be reconstructed. In contrast to the hybrid three-dimensional and two-dimensional temporal tracking approach, the use of two-dimensional planes allows much faster monitoring of the feature because it does not necessitate full sweeps on the structure, even if a full three-dimensional image is reconstructed any time there is a significant change in the feature.

Strategy 3: Hybrid three-dimensional and low-resolution three-dimensional temporal tracking.

In another approach, a series of alternating high (full three-dimensional) and low resolution ("targeted"), ultrasound sweeps are used to track the volume and followed with full volume reconstruction. Reducing the resolution allows for faster sweeps, but due to the limited frame-rate of the ultrasound, fewer two-dimensional slices are acquired for the reconstruction. For example, the high resolution three-dimensional images may be acquired at a periodicity of every thirty seconds, whereas the lower resolution images are obtained every 0.1-3 seconds. A new high-resolution image is captured for every period, unless the comparison between the high-resolution and low-resolution images indicated the violation of a displacement threshold, in which case a new high-resolution image is obtained sooner than would have been taken otherwise. In some cases, the displacement may be sufficient to halt treatment altogether and adjust the patient, the treatment device or both.

Strategy 4: Hybrid three-dimensional and limited ROI three-dimensional temporal tracking.

Figure 5:
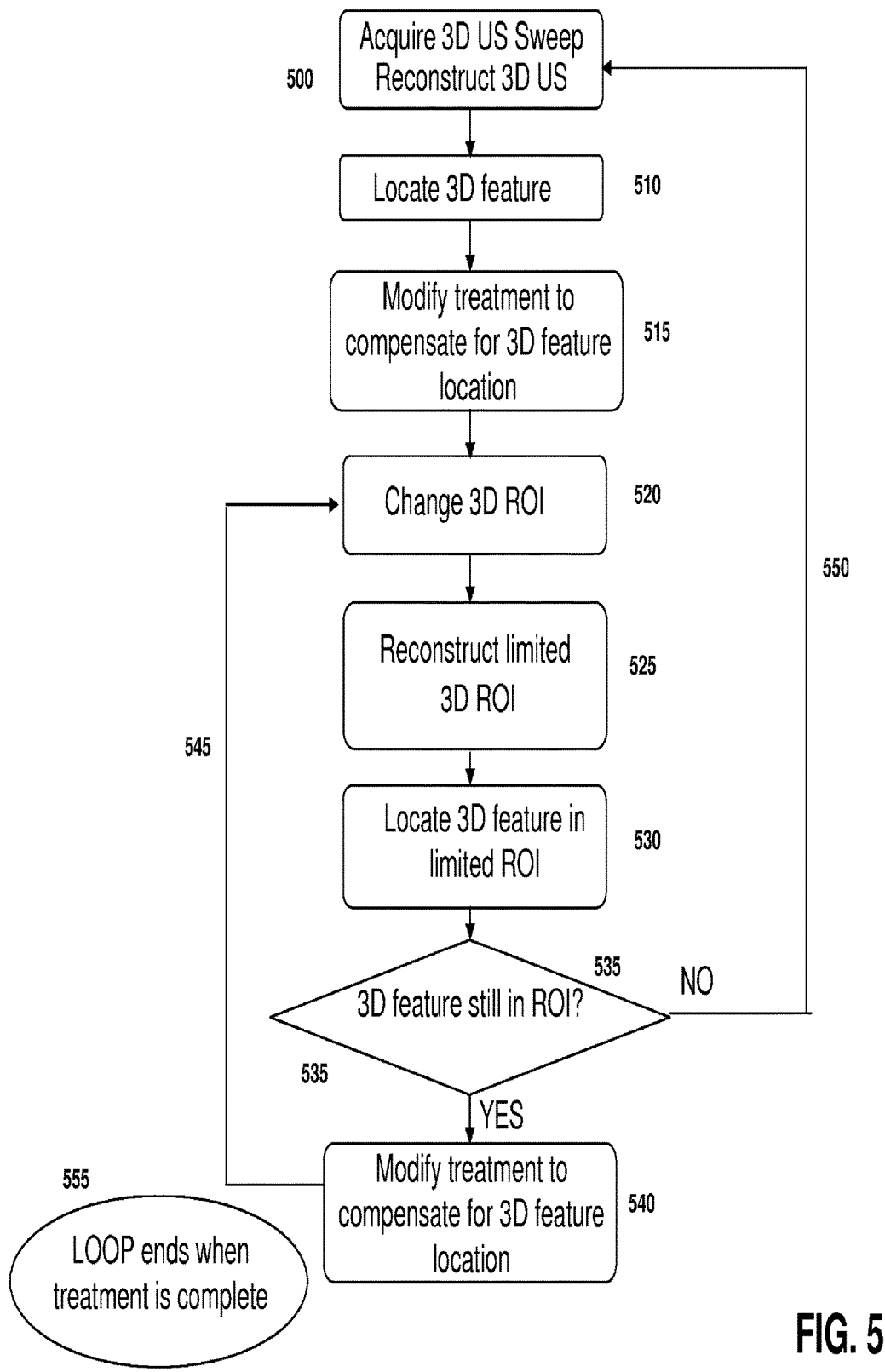
FIG. 5 is a flow-chart illustrating a particular implementation of a hybrid three-dimensional and limited ROI three-dimensional temporal tracking strategy according to various embodiments of the invention.
Figure 6:
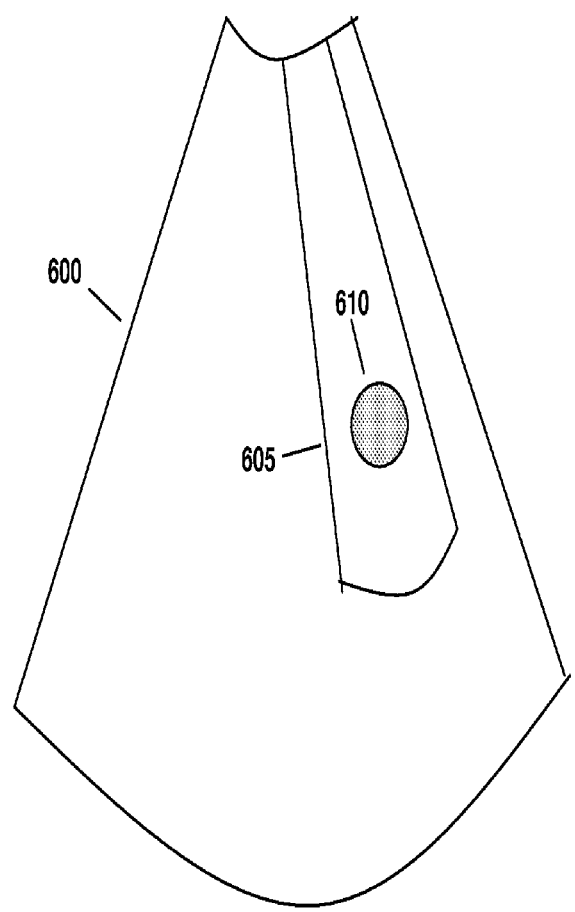
FIG. 6 illustrates a particular implementation of a hybrid three-dimensional and multiple two-dimensional plane temporal tracking in which the image extent encompassing the feature being treated is reduced according to various embodiments of the invention

FIG. 5 illustrates an alternative approach. Steps 500-515 are the same as steps 200-215 of FIG. 2, respectively. In step 520, the region of interest (ROI) of the three-dimensional volume is reduced such that it encompasses only the feature plus a limited amount of surrounding voxels. This is accomplished by limiting the sector size of the two-dimensional ultrasound frames throughout the sweep, in some cases asymmetrically, as well as the depth of penetration. Referring to FIG. 6 as an example, the full sector size and depth, leading to image extent 600, are reduced to form the image extent 605 which encompasses the feature 610 with a small amount of padding. Reducing sector size and/or depth increases the frame-rate, which allows for faster sweeping motion while still acquiring sufficient slices for high resolution three-dimensional image reconstruction. The range of X values for the sweeping motion can also be limited, which increases the three-dimensional image acquisition as well. Many more temporal three-dimensional images can be acquired, but due to the smaller region, the risk that the feature moves outside of the limited ROI increases.

Returning to FIG. 5, the limited three-dimensional ROI is reconstructed (step 525), and due to the smaller number of voxels, the speed of the reconstruction process is increased and the memory requirements are reduced as compared to a full three-dimensional reconstruction. In step 530, the location of the three-dimensional feature within the limited ROI is determined. In step 535, if the feature has remained in the limited ROI, step 545 is executed, continuing the tracking of the feature within the limited ROI. The ROI can be re-modified in step 520 to account for any new positioning of the feature. If the feature is no longer within the limited ROI, or getting too close to a boundary, then step 550 allows for a full ROI reconstruction prior to limiting the ROI again for further tracking. In some cases, full ROI sweeps are also acquired at various time intervals. The loop ends when treatment is complete, as represented by step 555.

Strategy 5: Hybrid three-dimensional and multiple two-dimensional plane temporal tracking with reduced sector size In another approach, two tracking planes are used—the first plane is a pure two-dimensional ultrasound at a fixed X position of the motorized probe as described above (the X position can be adjusted to include the tracked feature as its position is updated), and the second plane is a reconstructed plane which is orthogonal or near-orthogonal to the first plane. The ultrasound data in the second plane is acquired with a very small sector size, ideally approaching zero, so that the sweep can be performed quickly. In some variations, the sector size is very small during most of the sweep, is rapidly increased as the sweep crosses through X of the pure ultrasound plane, then reduced quickly again to complete the acquisition of reconstructed plane.

Locating an anatomical feature according to one or more of the methods descried above can be performed by drawing a structure (either manually, semi-automatically, or automatically) in a first image. This first image can, for example, be an image from a previous planning session, a previous treatment session, or an image obtained for a first interfractional motion correction prior to tracking. In most applications of interest, the structure being tracked does not change shape while the patient is on the table. Thus, the original structure can be moved from image to image, keeping its shape intact, so that it best-fits each image. The amount the structure is moved within an image provides a distance the feature has travelled between each successive image. If image acquisition is fast enough, motion between successive images is small and easier to track. This applies to both two-dimensional contours in planes as well as three-dimensional contours.

Although the specific applications above utilize a mechanized three-dimensional probe, other types of three-dimensional probes can be used as well. For example, matrix probes, which consist of a two-dimensional surface of piezoelectric elements, can acquire full three-dimensional ultrasound datasets. Bi-planar probes, which can simultaneously acquire two perpendicular slices of two-dimensional ultrasound data, can also be used in some embodiments.

Figure 7:
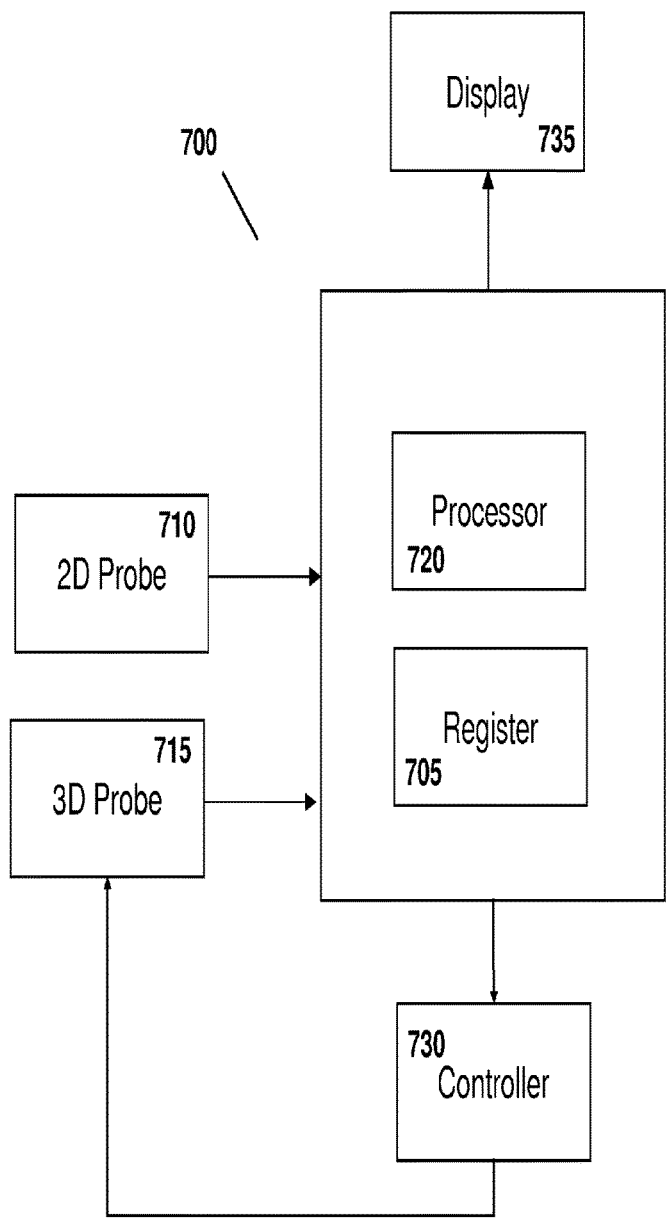
FIG. 7 illustrates a system for tracking intrafractional motion during the course of radiotherapy according to various embodiments of the invention.

Referring to FIG. 7, a system 700 for performing the techniques described above includes a register 705 or other volatile or non-volatile storage device that receives image data from the ultrasound imaging probe(s) 710 and/or 715 via a cord or wire, or in some embodiments via wireless communications. The system also includes a processor 720 that, based on the image data, uses the techniques described above to create three-dimensional, time-based images of the region of interest and determine if the feature being treated has moved and/or morphed such that the displacement or changes in shape or size require adjustments to image parameters used to capture subsequent images. The processor calculates any necessary adjustments and, in some cases, provides updated imaging parameters to a controller 730. The controller 730 directs the probe(s) 710 and/or 715 to implement the adjustments either mechanically (e.g., by changing the physical location of the probe within its housing or implementing positional adjustments directly or using a brace, arm or other support device) or electronically (e.g., by altering the power delivered to the probes and/or frequency of the ultrasound energy). As such, the feature remains in the region being imaged throughout the entire imaging and treatment process.

In some embodiments, a display 735 and an associated user interface may also be included, thus allowing a user to view and manipulate the images and/or treatment parameters. The display 735 and user interface can be provided as one integral unit (as shown) or separate units and may also include one or more user input devices such as a keyboard and/or mouse. The display can be passive (e.g., a "dumb" CRT or LCD screen) or in some cases interactive, facilitating direct user interaction with the images and models through touch-screens (using, for example, the physician's finger as an input device) and/or various other input devices such as a stylus, light pen, or pointer. The display 735 and input devices may be in location different from that of the register 705 and/or processor 720, thus allowing users to receive, view, and manipulate images in remote locations using, for example, wireless devices, handheld personal data assistants, notebook computers, among others.

In various embodiments the register and/or processor may be provided as either software, hardware, or some combination thereof. For example, the system may be implemented on one or more server-class computers, such as a PC having a CPU board containing one or more processors such as the Pentium or Celeron family of processors manufactured by Intel Corporation of Santa Clara, Calif., the 680x0 and POWER PC family of processors manufactured by Motorola Corporation of Schaumburg, Ill., and/or the ATHLON line of processors manufactured by Advanced Micro Devices, Inc., of Sunnyvale, Calif. The processor may also include a main memory unit for storing programs and/or data relating to the methods described above. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, as well as other commonly storage devices.

For embodiments in which the invention is provided as a software program, the program may be written in any one of a number of high level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

It will therefore be seen that the foregoing represents an improved method and supporting system for tracking features over the course of a medical procedure. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Moreover, although the above-listed text and drawings contain titles headings, it is to be understood that these title and headings do not, and are not intended to limit the present invention, but rather, they serve merely as titles and headings of convenience.

The invention claimed is:

1. A method of using a processor circuit executing a plurality of computer-executable instructions for monitoring one or more anatomical features of a patient, comprising:
    controlling an ultrasound imaging probe to acquire first three-dimensional image data including a first three-dimensional image of a volume of interest including at least one of the anatomical features;
    locating a three-dimensional feature, corresponding to the at least one anatomical feature, within the first three-dimensional image;
    based on a surface of the three-dimensional feature, controlling the ultrasound imaging probe to acquire a first two-dimensional image along a first plane position that intersects a region of the three-dimensional feature;
    based on the first two-dimensional image, determining displacement of the three-dimensional feature relative to a previous point in time; and
    controlling the ultrasound imaging probe to change the first plane position for subsequent two-dimensional image capture based on the determined displacement.

2. The method of claim 1, comprising:
    controlling the ultrasound imaging probe to acquire two or more two-dimensional images that include the region of interest;
    locating the at least one two-dimensional feature in each of the two or more two-dimensional images;
    and
    estimating a corresponding displacement of the three-dimensional feature using the two-dimensional features.

3. The method of claim 1, further comprising:
    determining whether the three-dimensional feature is visible in a given two-dimensional image acquired by the ultrasound imaging probe;
    in response to determining that the three-dimensional feature is not visible in the given two-dimensional image, reconstructing a second three-dimensional image of the volume of interest.

4. The method of claim 1, wherein the first two-dimensional image comprises a reconstructed image generated using an acquired plurality of two-dimensional images corresponding to one or more of different imaging probe positions or different imaging probe orientations.

5. The method of claim 1, wherein the first two-dimensional image comprises a two-dimensional image acquired according to one or more of a specified imaging probe position or a specified imaging probe orientation.

6. The method of claim 1, comprising determining whether the displacement of the three-dimensional feature meets or exceeds a predetermined threshold.

7. The method of claim 6, wherein controlling the ultrasound imaging probe to alter the parameter for acquisition of image data includes controlling the ultrasound imaging probe to acquire second three-dimensional image data including a second three-dimensional image when the displacement of the three-dimensional feature meets or exceeds the predetermined threshold.

8. The method of claim 7, comprising controlling the ultrasound imaging probe to acquire the first three-dimensional image data and the second three-dimensional image data at a first image acquisition rate.

9. The method of claim 8, wherein controlling the ultrasound imaging probe to acquire the first two-dimensional image includes controlling the ultrasound imaging probe to acquire two-dimensional image data including a plurality of two-dimensional images at a second image acquisition rate.

10. The method of claim 9, wherein the second image acquisition rate is greater than the first image acquisition rate.

11. The method of claim 6, comprising controlling the ultrasound imaging probe to acquire two-dimensional image data including an additional two-dimensional image when the displacement of the three-dimensional feature does not meet or exceed the predetermined threshold.

12. The method of claim 1, wherein the first plane position intersects a center of the region of the three-dimensional feature, further comprising:
    based on the surface of the three-dimensional feature, controlling the ultrasound imaging probe to acquire a second two-dimensional image along a second plane position that intersects a portion of the region of the three-dimensional feature offset from the center of the region;
    producing a two-dimensional curve based on an intersection of the first and second planes of the first and second two-dimensional images and the three-dimensional feature;
    determining where the two-dimensional curve best fits grayscale values of the three-dimensional feature to determine the displacement.

13. The method of claim 12, wherein the first three-dimensional image data and the first two-dimensional image are acquired using ultrasound signals, and wherein the first and second planes are orthogonal.

14. A system for controlling an ultrasound imaging probe to monitor an anatomical feature of a patient, comprising:
    a memory circuit for storing instructions and image data; and
    a processor circuit for executing the instructions to:
        control the ultrasound imaging probe to acquire first three-dimensional image data from the ultrasound imaging probe including a first three-dimensional image of a volume of interest including the anatomical feature;
        locate a three-dimensional feature, corresponding to the at least one anatomical feature, within the first three-dimensional image;
        based on a surface of the three-dimensional feature, control the ultrasound imaging probe to acquire a first two-dimensional image along a first plane position that includes intersects a region of the three-dimensional feature;
        based on the first two-dimensional image, determine displacement of the three-dimensional feature relative to a previous point in time; and
        control the ultrasound imaging probe to change the first plane position for subsequent two-dimensional image capture based on the determined displacement.

15. The system of claim 14, wherein the instructions cause the processor circuit to:
control the ultrasound imaging probe to acquire two or more two-dimensional images that include the region of interest;
locate the at least one two-dimensional feature in each of the two or more two-dimensional images; and
estimate a corresponding displacement of the three-dimensional feature using the two-dimensional features.

16. The system of claim 14, wherein the first plane position intersects a center of the region of the three-dimensional feature, and wherein the instructions cause the processor circuit to:
based on the surface of the three-dimensional feature, control the ultrasound imaging probe to acquire a second two-dimensional image along a second plane position that intersects a portion of the region of the three-dimensional feature offset from the center of the region;
produce a two-dimensional curve based on an intersection of the first and second planes of the first and second two-dimensional images and the three-dimensional feature;
determine where the two-dimensional curve best fits grayscale values of the three-dimensional feature to determine the displacement.

17. The system of claim 14, wherein the instructions cause the processor circuit to:
determine whether the three-dimensional feature is visible in a given two-dimensional image acquired by the ultrasound imaging probe;
in response to determining that the three-dimensional feature is not visible in the given two-dimensional image, reconstruct a second three-dimensional image of the volume of interest.

18. The system of claim 14, wherein the instructions cause the processor circuit to:
control the ultrasound imaging probe to acquire two-dimensional image data including a plurality of two-dimensional images at a two-dimensional acquisition rate; and
control the ultrasound imaging probe to acquire the first three-dimensional image data and the second three-dimensional image data at a three-dimensional acquisition rate, wherein the two-dimensional acquisition rate is greater than the three-dimensional acquisition rate.

19. The system of claim 14, wherein the first two-dimensional image comprises a reconstructed image generated using an acquired plurality of two-dimensional images corresponding to one or more of different imaging probe positions or different imaging probe orientations.

20. The system of claim 14, wherein the first two-dimensional image comprises a two-dimensional image acquired according to one or more of a specified imaging probe position or a specified imaging probe orientation.

21. The system of claim 14, wherein the instructions cause the processor circuit to obtain second three-dimensional image data including a second three-dimensional image when the displacement meets or exceeds the threshold.

22. The system of claim 21, wherein the instructions cause the processor circuit to control the ultrasound imaging probe to acquire additional two-dimensional image data including an additional two-dimensional image when the displacement does not meet or exceed the threshold.

23. A non-transitory computer-readable medium comprising instructions, which, when executed by a processor circuit, cause the processor circuit to control an ultrasound imaging probe to monitor one or more anatomical features of a patient, the medium comprising instructions to:
control the ultrasound imaging probe to acquire first three-dimensional image data including a first three-dimensional image of a volume of interest including at least one of the anatomical features;
locate a three-dimensional feature within the three-dimensional image corresponding to the at least one anatomical feature;
based on a surface of the three-dimensional feature, control the ultrasound imaging probe to acquire a first two-dimensional image along a first plane position that intersects a region of the three-dimensional feature;
based on the first two-dimensional image, determine displacement of the three-dimensional feature relative to a previous point in time; and
control the ultrasound imaging probe to change the first plane position for subsequent two-dimensional image capture based on the determined displacement.

24. The non-transitory computer-readable medium of claim 23, wherein the one or more anatomical features of a patient comprise at least one of a target lesion, a subset of a target lesion, an implanted fiducial, a surface fiducial, an implanted fiducial seed, or combinations thereof.

25. The non-transitory computer-readable medium of claim 23, wherein the medium further comprises instructions to:
based on the surface of the three-dimensional feature, control the ultrasound imaging probe to acquire a second two-dimensional image along a second plane position that intersects a portion of the region of the three-dimensional feature offset from the center of the region;
produce a two-dimensional curve based on an intersection of the first and second planes of the first and second two-dimensional images and the three-dimensional feature;
determine where the two-dimensional curve best fits grayscale values of the three-dimensional feature to determine the displacement.

26. The non-transitory computer-readable medium of claim 23, wherein the first two-dimensional image comprises a reconstructed image generated using an acquired plurality of two-dimensional images corresponding to one or more of different imaging probe positions or different imaging probe orientations.

27. The non-transitory computer-readable medium of claim 23, wherein the at least one three-dimensional image comprises a reconstructed image generated using an acquired plurality of images corresponding to one or more of different imaging probe positions or different imaging probe orientations.

28. The non-transitory computer-readable medium of claim 23, wherein the first two-dimensional image comprises a two-dimensional image acquired according to one or more of a specified imaging probe position or a specified imaging probe orientation.

* * * * *

UNITED STATES PATENT AND TRADEMARK OFFICE
CERTIFICATE OF CORRECTION

PATENT NO. : 10,449,390 B2
APPLICATION NO. : 14/702037
DATED : October 22, 2019
INVENTOR(S) : Lachaine et al.

Page 1 of 1

It is certified that error appears in the above-identified patent and that said Letters Patent is hereby corrected as shown below:

In the Claims

In Column 14, Line 59, in Claim 14, after "that", delete "includes"

Signed and Sealed this
Nineteenth Day of May, 2020

Andrei Iancu
*Director of the United States Patent and Trademark Office*